US006762021B2

(12) United States Patent
Tokunaga et al.

(10) Patent No.: US 6,762,021 B2
(45) Date of Patent: Jul. 13, 2004

(54) METHOD FOR DIAGNOSIS OF CROHN'S DISEASE

(75) Inventors: Katsushi Tokunaga, Tokyo (JP); Naoyuki Tsuchiya, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 138 days.

(21) Appl. No.: 09/725,752

(22) Filed: May 22, 2001

(65) Prior Publication Data

US 2002/0081585 A1 Jun. 27, 2002

(30) Foreign Application Priority Data

May 31, 2000 (JP) ........................................ 2000-162858

(51) Int. Cl.$^7$ .......................... C12Q 1/68; C12P 19/34; C07H 21/04; C12N 9/02; C12N 9/12
(52) U.S. Cl. ..................... 435/6; 435/91.2; 435/91.51; 435/189; 435/194; 435/196; 536/23.2; 536/23.5; 536/24.31; 530/350
(58) Field of Search ..................... 435/6, 91.2, 91.51, 435/189, 194, 196; 536/23.2, 23.5, 24.31; 530/350

(56) References Cited

PUBLICATIONS

Engstrand, L. *Mycobacterium paratuberculosis* and Crohn's disease. Scandinavian Journal of Infectious Disease 98(Suppl):27–29 (1995).*
Solis–Herruzo, J.A. et al. Diminished cytochrome b content and toxic oxygen metabolite production in circulating neutrophils from patients with Crohn's disease. Digestive Diseases and Sciences 38(9):1631–1637 (Sep. 1993).*
K. Hagiwara et al., "Identification of genes expressed in the intestinal lesions of Crohn disease by differentiation display method", Proceedings of the Japanese Society for Immunology, vol. 29, 1999, p. 176 and its English translation thereof.
M. Filali et al., "Identification of a Type 6 Protein Ser/Thr Phosphatase Regulated by Interleukini–2 Stimulation", Journal of Cellular Biochemistry, vol. 73, No. 2, 1999, pp. 153–163.
C. Alan Fu et al., "TNIK, a Novel Member of the Germinal Center Kinase Family that Activates the c–Jun N–terminal Kinase Pathway and Regulates the Cytoskeleton", The Journal of Biological Chemistry, vol. 274, No. 43, Oct. 22, 1999, pp. 30729–30737.
M. Irmler et al., "Inhibition of Death Receptor Signals by Cellular FLIP", Nature, vol. 388, Jul. 10, 1997, pp. 190–195.
S. Hollenberg et al., "Primary Structure and Expression of a Functional Human Glucocorticoid Receptor cDNA", Nature, vol. 318, Dec. 1985, pp. 635–641.
F. Sanger et al., "Cloning in Single–Stranded Bacteriophage as an Aid to Rapid DNA Sequencing", J. Mol. Biol. vol. 143, 1980 pp. 161–178.
S. Anderson et al., "Sequence and Organization of the Human Mitochondrial Genome", Nature, vol. 290, Apr. 9, 1981, pp. 457–465.
Report presented in the 29$^{th}$ Annual Meeting of the Japanese Society for Immunology Dec. 2, 1999. (English translation) (vol./pp./No. NA).

* cited by examiner

Primary Examiner—Diana B. Johannsen
(74) Attorney, Agent, or Firm—Wenderoth, Lind & Ponack, L.L.P.

(57) ABSTRACT

The present invention provides a reagent for diagnosing Crohn's disease, which contains at least one member selected from the group consisting of a group of substances having a specific affinity for a protein (or a gene thereof) whose expression is potentiated in a lesion-specific manner, such as a substance having a specific affinity for PP6 regulated by IL-2 (or a gene thereof), a substance having a specific affinity for TNIK (or a gene thereof), a substance having a specific affinity for FLIP (or a gene thereof), a substance having a specific affinity for GRα (or a gene thereof) and the like. By taking note of a gene whose expression is potentiated in a lesion-specific manner, and examining the behavior thereof by the use of this diagnostic reagent, the disease can be diagnosed easily and quickly.

2 Claims, No Drawings

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF PP6
      REGULATED BY IL-2 mRNA

<400> SEQUENCE: 1
acccattttt ctgccctctt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF PP6 BY
      IL-2 mRNA

<400> SEQUENCE: 2
tcgtgcccac tgaataacaa                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF TNIK mRNA

<400> SEQUENCE: 3
tggttcacac actggtttcc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF TNIK mRNA

<400> SEQUENCE: 4
ccggccatag gtgtttacat                                              20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF FLIPL mRNA

<400> SEQUENCE: 5
ctccaagcag caatccaaa                                               19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF FLIPL mRNA -continued

```
<400> SEQUENCE: 6
gattcctagg ggcttgctct                                                    20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF FLIPL mRNA

<400> SEQUENCE: 7
tgcctaaaga acatccacag aa                                                 22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF FLIPS mRNA

<400> SEQUENCE: 8
cacatggaac aatttccaag aa                                                 22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF GR a mRNA

<400> SEQUENCE: 9
cctaaggacg gtctcaagag c                                                  21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF GR a mRNA

<400> SEQUENCE: 10
gccaagtctt ggccctctat                                                    20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF CYTOCHROME
      OXIDASE SUBUNIT I

<400> SEQUENCE: 11
acgcactctc ccctgaact                                                     19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF CYTOCHROME
```

-continued

OXIDASE SUBUNIT I

<400> SEQUENCE: 12
ggggaatgct ggagattgta                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF
      CYCTOCHROME b mRNA

<400> SEQUENCE: 13
cacatcaagc ccgaatgata                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE DESIGNED TO ACT AS PRIMER FOR RT-PCR OF CYTOCHROME
      b mRNA

<400> SEQUENCE: 14
gtctgcggct aggagtcaat                                                    20

METHOD FOR DIAGNOSIS OF CROHN'S DISEASE

TECHNICAL FIELD OF THE INVENTION

The present invention relates to a diagnostic reagent and a method for diagnosing Crohn's disease.

BACKGROUND OF THE INVENTION

Autoimmune diseases refer to a phenomenon wherein a biological defense system (immune system) attacks the cells of its own. Antibodies and lymphocytes reactive with the autoantigen are derived, which in turn develops tissue disorders and lesions. The autoimmune diseases are generally divided into two groups: those without organ specificity and those with organ specificity. The mechanism of the onset of the autoimmune diseases is mostly unclear, though involvement of autoimmunity is suggested. There are many problems to be solved such as diagnosis method and the like, which include the mechanism of the onset of autoimmune diseases.

The autoimmune diseases include Crohn's disease, as one of the diseases whose etiology has not been elucidated, in which an immune reaction against autoantigen and allergy are considered to be involved. This disease is an inflammatory bowel disease associated with inflammatory changes throughout the full thickness of the wall of the digestive tract, discontinuous deep ulcer and histologically noncaseating granuloma. The skipping of the lesion also characterizes this disease. The definite diagnosis of Crohn's disease is based on a comprehensive observation of the disease state, X rays, endoscopy and tissue images. However, since the diagnosis is possible only after the progress of the disease, earlier diagnosis is desired. In addition, differential diagnosis from other inflammatory bowel diseases, such as acute or chronic appendicitis, tuberculosis of the intestine, ulcerative colitis, ischemic enteritis and the like, is required.

There are reports documenting that the genes of membrane proteins such as interleukin 2 (IL-2) receptor, transferrin receptor, E-selectin (also referred to as ELAM-1, endothelial leukocyte adhesion molecule-1), VCAM-1 (vascular cell adhesion molecule-1), L-selectin, CD11, OX40, OX40 ligand and the like, and cytokines and chemokines such as interleukin 1β (IL-1β), IL-2, interleukin 6 (IL-6), interleukin 15 (IL-15), tumor necrosis factor α (TNF-α), interleukin 18 (IL-18), interleukin 8 (IL-8), MCP-1, ENA-78 and the like are up-regulated in Crohn's disease, from a molecular biological approach taking note of the expression of cytokines and adhesion molecules. However, most of these genes in the reports showed the up-regulation due to a non-specific immune response associated with the inflammation observed in Crohn's disease, and the up-regulation is not specific to Crohn's disease.

SUMMARY OF THE INVENTION

It is therefore an object of the present invention to provide a method useful for diagnosing Crohn's disease and a reagent for the diagnosis.

In view of the above-mentioned problems, the present inventors have conducted intensive studies of the expression profiles at the gene level of Crohn's disease, in an attempt to enable early diagnosis of Crohn's disease and differential diagnosis from other diseases. Since a lesion and a non-lesion part can be clearly distinguished visually in Crohn's disease, a differential display method (Liang, P., and Pardee, A. B. Science 257:967–971 (1992), Liang, P., and Pardee, A. B. Curr. Opin. Immunol. 7:274–280 (1995)), wherein the genes expressed in the lesion and the non-lesion part in the same individual can be compared, was employed to compare gene expression profiles in the lesion and the non-lesion part. As a result, the expression of a certain kind of gene in the lesion was found to have been specifically potentiated and the gene could be identified, which resulted in the completion of the present invention.

Accordingly, the present invention provides the following.

(1) A reagent for diagnosing Crohn's disease, which contains at least one member selected from the group consisting of (i) a substance having a specific affinity for a gene of a type 6 protein phosphatase regulated by interleukin 2 (type 6 protein phosphatase regulated by IL-2; hereinafter to be also referred to as PP6 regulated by IL-2), (ii) a substance having a specific affinity for a gene of a Traf 2 and Nck interacting kinase (hereinafter to be also referred to as TNIK), (iii) a substance having a specific affinity for a gene of a FLICE inhibitory protein (hereinafter to be also referred to as FLIP), and (iv) a substance having a specific affinity for a gene of a glucocorticoid receptor α (hereinafter to be also referred to as GRα).

(2) The reagent for diagnosing Crohn's disease according to the above-mentioned mentioned (1), which further contains at least one member selected from the group consisting of (v) a substance having a specific affinity for a cytochrome oxidase subunit I gene and (vi) a substance having a specific affinity for a cytochrome b gene.

(3) The reagent for diagnosing Crohn's disease according to the above-mentioned (1) or (2), wherein the substance having a specific affinity is an oligonucleotide or polynucleotide probe, or an oligonucleotide or polynucleotide primer pair.

(4) A reagent for diagnosing Crohn's disease, which contains at least one member selected from the group consisting of (i) a substance having a specific affinity for PP6 regulated by IL-2, (ii) a substance having a specific affinity for TNIK, (iii) a substance having a specific affinity for FLIP, and (iv) a substance having a specific affinity for GRα.

(5) The reagent for diagnosing Crohn's disease according to the above-mentioned (4), which further contains at least one member selected from the group consisting of (v) a substance having a specific affinity for a cytochrome oxidase subunit I and (vi) a substance having a specific affinity for cytochrome b.

(6) The reagent for diagnosing Crohn's disease according to the above-mentioned (4) or (5), wherein the substance having a specific affinity is an antibody or a fragment thereof.

(7) A method for diagnosing Crohn's disease, which comprises the steps of
  (a) taking a biological sample from an animal that developed or is associated with a risk of developing Crohn's disease, and
  (b) analyzing the expression of at least one gene selected from the group consisting of a gene of PP6 regulated by IL-2, a TNIK gene, a FLIP gene and a GRα gene, in a biological sample thereof.

(8) The method for diagnosing Crohn's disease according to the above-mentioned (7), which further includes analyzing the expression of at least one gene selected from the group consisting of a cytochrome oxidase subunit I gene and a cytochrome b gene.

(9) A method for diagnosing Crohn's disease, which comprises the steps of
  (a) taking a biological sample from an animal that developed or is associated with a risk of developing Crohn's disease, and
  (b) analyzing the expression of at least one protein selected from the group consisting of PP6 regulated by IL-2, TNIK, FLIP and GRα, in a biological sample thereof.
(10) The method for diagnosing Crohn's disease according to the above-mentioned (9), which further includes analyzing the expression of at least one protein selected from the group consisting of cytochrome oxidase subunit I and cytochrome b.
(11) The method for diagnosing Crohn's disease according to any of the above-mentioned (7) to (10), wherein the biological sample is an ileum tissue or colon tissue derived from the animal.

DETAILED DESCRIPTION OF THE INVENTION

The gene in the present invention may be of any form unless otherwise particularly specified. For example, complementary DNA (cDNA) prepared from mRNA and the like are included besides mRNA.

The respective elements that may be contained in the diagnostic reagent according to the present invention are explained in detail in the following.

(i) PP6 Regulated by IL-2 [Type 6 Protein Phosphatase Regulated by IL-2; Protein (36 kDa) described in Filali, M., et al., J. Cell. Biochem. 73:153–163 (1999)]

The PP6 regulated by IL-2 is a phosphoprotein having a 98% homology to human PP6 at the amino acid level, and its expression is derived by IL-2 in the peripheral T cell. Its precise function has not been elucidated but involvement in the cell proliferation is suggested (Filali, M., et al., (1999) ibid.).

Examples of the substance having a specific affinity for the gene of PP6 regulated by IL-2, which is contained in the reagent for diagnosing Crohn's disease of the present invention, include an oligonucleotide or polynucleotide probe (hereinafter to be conveniently referred to simply as a probe) having a specific affinity for the gene, and an oligonucleotide or polynucleotide primer pair (hereinafter to be conveniently referred to simply as a primer pair), wherein the specific affinity for the gene means the ability to specifically hybridize only to the objective gene. Therefore, the probe and the primer pair may be completely complementary to the entire gene or a part thereof, or may include one to several mismatches as long as they have the above-mentioned property. The probe and the primer pair are not subject to any particular limitation as long as they have specific affinity for the gene. Examples thereof include the entire nucleotide sequence of the gene or a part thereof, an oligonucleotide or polynucleotide containing a sequence complementary thereto, and the like, which may be selected as appropriate depending on the form of the gene to be detected. When PCR and the like are conducted as mentioned later using the diagnostic reagent of the present invention, the oligonucleotides depicted in SEQ ID NO. 1 and SEQ ID NO. 2 can be used as primer pairs. The origins of oligonucleotide and polynucleotide are not subject to any particular limitation as long as they have specific affinity for the gene. They may be synthesized or obtained by cleaving out the necessary portion from the gene, and purifying it according to a typical method. These oligonucleotide and polynucleotide may be labeled with a fluorescent substance, enzyme, radioisotope and the like.

Examples of the substance having a specific affinity for PP6 regulated by IL-2, which is contained in the reagent for diagnosing Crohn's disease of the present invention, include an antibody having a specific affinity for the protein and a fragment thereof, wherein the specific affinity means the ability to specifically recognize the protein by an antigen-antibody reaction and to bind therewith. Such antibody and the fragment thereof are not subject to any particular limitation as long as they can specifically bind with the protein, and may be a polyclonal antibody, a monoclonal antibody or an operable fragment thereof. These antibodies and operable fragments thereof can be produced by a method generally employed in the pertinent field. When a polyclonal antibody is used, for example, an animal such as mouse and rabbit is immunized by injecting the protein subcutaneously to the back, intraperitoneally or into the vein and the like, and antiserum is harvested after increase in the antibody titer. When a monoclonal antibody is used, a hybridoma is prepared by a conventional method and a secretion thereby is taken. The antibody fragment is often produced by the expression, by a microorganism and the like, of a cloned gene fragment of an antibody. The purity of the antibody, antibody fragment and the like is not subject to any particular limitation as long as they can maintain the specific affinity for the protein. These antibodies and fragments thereof may be labeled with a fluorescent substance, enzyme, radioisotope and the like.

Furthermore, these may be obtained from the market.

(ii) TNIK [Traf2 and Nck Interacting Kinase; GCK Family Kinase described in Fu, C. A., et al., J. Biol. Chem. 274:30729–30737 (1999)]

The TNIK is a kinase that interacts with both Traf2 and Nck, and has been recently identified as a molecule that activates JNK.

Examples of the substance having a specific affinity for the TNIK gene, which is contained in the reagent for diagnosing Crohn's disease according to the present invention, include a probe and a primer pair having a specific affinity for the gene, wherein specific affinity for the gene means as mentioned above. The probe and the primer pair can be designed and modified based on the nucleotide sequence of the gene, as explained in the section for the above-mentioned PP6 regulated by IL-2. When PCR and the like are conducted using the diagnostic reagent of the present invention, the oligonucleotides depicted in SEQ ID NO. 3 and SEQ ID NO. 4 can be used as primer pairs.

Examples of the substance having a specific affinity for TNIK, which is contained in the reagent for diagnosing Crohn's disease according to the present invention, include an antibody having a specific affinity for the protein and a fragment thereof, wherein the specific affinity for the protein means as mentioned above. These antibodies and operable fragments thereof can be produced by a method similar to the general method explained in the section for the above-mentioned PP6 regulated by IL-2.

(iii) FLIP [FLICE inhibitory protein; described in Irmler, M., et al., Nature 388:190–195 (1997), Human FLIP$_L$: Gen- Bank Accession No. U97074, human FLIP$_S$: GenBank Accession No. U97075]

The FLIP is a structural analog of FLICE, which is reported to suppress apoptosis by inhibiting association of FADD and FLICE (Irmler, M., et al., (1997) ibid., Hu, S., et al., J. Biol. Chem. 272:17255–17257 (1997)). It includes a long form (FLIP$_L$) and a short form (FLIP$_s$).

Examples of the substance having a specific affinity for the FLIP gene, which is contained in the reagent for diagnosing Crohn's disease according to the present invention, include a probe and a primer pair having a specific affinity for the gene, wherein the specific affinity for the gene means as mentioned above. The probe and the primer pair can be designed and modified based on the nucleotide sequence of the gene, as explained in the section for the above-mentioned PP6 regulated by IL-2. When PCR and the like are conducted using the diagnostic reagent of the present invention, the oligonucleotides depicted in SEQ ID NO. 5 and SEQ ID NO. 6 can be used as primer pairs for FLIP$_L$, and those depicted in SEQ ID NO. 7 and SEQ ID NO. 8 for FLIP$_s$.

Examples of the substance having a specific affinity for FLIP, which is contained in the reagent for diagnosing crohn's disease according to the present invention, include an antibody having a specific affinity for the protein and a fragment thereof, wherein the specific affinity for the protein means as mentioned above. These antibodies and operable fragments thereof can be produced by a method similar to the general method explained in the section for the above-mentioned PP6 regulated by IL-2.

(iv) GRα [Glucocorticoid Receptor α; Protein (94 kDa) described in Hollenberg, S. M., et al., Nature 318:635–641 (1985)]

The GRα is a receptor belonging to a nuclear receptor superfamily, wherein ligand is glucocorticoid, and is a transcriptional regulatory factor that promotes transcription of the target gene in a ligand-dependent manner.

Examples of the substance having a specific affinity for the GRα gene, which is contained in the reagent for diagnosing Crohn's disease according to the present invention, include a probe and a primer pair having a specific affinity for the gene, wherein the specific affinity for the gene means as mentioned above. The probe and the primer pair can be designed and modified based on the nucleotide sequence of the gene, as explained in the section for the above-mentioned PP6 regulated by IL-2. When PCR and the like are conducted using the diagnostic reagent of the present invention, the oligonucleotides depicted in SEQ ID NO. 9 and SEQ ID NO. 10 can be used as primer pairs.

Examples of the substance having a specific affinity for GRα, which is contained in the reagent for diagnosing Crohn's disease according to the present invention, include an antibody having a specific affinity for the protein and a fragment thereof, wherein the specific affinity for the protein means as mentioned above. These antibodies and operable fragments thereof can be produced by a method similar to the general method explained in the section for the above-mentioned PP6 regulated by IL-2.

(v) Cytochrome Oxidase Subunit I [described in Sanger, F., et al., J. Mol. Biol. 143(2), 161–178 (1980), Anderson, S., et al., Nature 290 (5806), 457–465 (1981)]

The cytochrome oxidase is a terminal oxidase of an electron transfer system present in the mitochondrial inner membrane, and consists of 7 to 13 subunits. This enzyme is essential for synthesizing ATP from ADP and inorganic phosphorus. The NO produced in the inflamed area is known to bind with the cytochrome oxidase subunit I competitively with an oxygen molecule.

Examples of the substance having a specific affinity for the cytochrome oxidase subunit I gene, which is contained in the reagent for diagnosing Crohn's disease according to the present invention, include a probe and a primer pair having a specific affinity for the gene, wherein the specific affinity for the gene means as mentioned above. The probe and the primer pair can be designed and modified based on the nucleotide sequence of the gene, as explained in the section for the above-mentioned PP6 regulated by IL-2. When PCR and the like are conducted using the diagnostic reagent of the present invention, the oligonucleotides depicted in SEQ ID NO. 11 and SEQ ID NO. 12 can be used as primer pairs.

Examples of the substance having a specific affinity for cytochrome oxidase subunit I, which is contained in the reagent for diagnosing Crohn's disease according to the present invention, include an antibody having a specific affinity for the protein and a fragment thereof, wherein the specific affinity for the protein means as mentioned above. These antibodies and operable fragments thereof can be produced by a method similar to the general method explained in the section for the above-mentioned PP6 regulated by IL-2.

(vi) Cytochrome b [described in Anderson, S., et al., Nature 290 (5806), 457–465 (1981)]

The cytochrome refers to a group of heme protiens responsible for the electron transfer. The cytochrome b is present in a mitochondrial inner membrane along with c1, a3 and the like, and constitutes an electron transfer system.

Examples of the substance having a specific affinity for the cytochrome b gene, which is contained in the reagent for diagnosing Crohn's disease according to the present invention, include a probe and a primer pair having a specific affinity for the gene, wherein the specific affinity for the gene means as mentioned above. The probe and the primer pair can be designed and modified based on the nucleotide sequence of the gene, as explained in the section for the above-mentioned PP6 regulated by IL-2. When PCR and the like are conducted using the diagnostic reagent of the present invention, the oligonucleotides depicted in SEQ ID NO. 13 and SEQ ID NO. 14 can be used as primer pairs.

Examples of the substance having a specific affinity for cytochrome b, which is contained in the reagent for diagnosing Crohn's disease according to the present invention, include an antibody having a specific affinity for the protein and a fragment thereof, wherein the specific affinity for the protein means as mentioned above. These antibodies and operable fragments thereof can be produced by a method similar to the general method explained in the section for the above-mentioned PP6 regulated by IL-2.

The respective elements (the above-mentioned (i)–(vi)), which are contained in the reagent for diagnosing Crohn's disease according to the present invention, can be used alone. Preferably, the reagent contains at least one of or all of the above-mentioned (i) to (iv) having higher specificity to Crohn's disease, i.e., a substance having a specific affinity for PP6 regulated by IL-2 and a gene of PP6 regulated by IL-2, a substance having a specific affinity for TNIK and its gene, a substance having a specific affinity for FLIP and its gene, and a substance having a specific affinity for GRα and its gene. Where desired, it may contain at least one of the above-mentioned (v) and (vi), i.e., a substance having a specific affinity for cytochrome oxidase subunit I and its gene and a substance having a specific affinity for cytochrome b and its gene. When plural substances are used, they may be admixed and used as one reagent or may be used as separate reagents. Even when plural substances are admixed and used as one reagent, it can easily distinguish each expression, based on the molecular weight of the objective protein or the length of the objective gene. However, particularly when the gene expression profiles of Crohn's disease (diagnostic subjects) show interindividual differences, and when a quick and easy diagnosis of Crohn's disease is desired, respective substances are preferably admixed and used as a single reagent. When a diagnosis including a detailed future treatment policy is desired, a diagnostic reagent containing one of the elements is preferably used.

The present invention also provides a method for diagnosing Crohn's disease. The diagnostic method of the present invention is preferably applied using the aforementioned diagnostic reagent for Crohn's disease. To be specific, a biological sample is first taken from an animal to be a diagnosis target. In this specification, by the "animal" is meant various mammals inclusive of human and birds. Examples thereof include human, monkey, dog, cat, cow, horse, pig, mouse, rabbit, chicken and the like. The biological sample is not subject to any particular limitation as long as it affords observation of noticeable changes in the expression of the above-mentioned various genes and proteins. Examples thereof include cell, tissue, urine, blood and the like taken from a body. Preferable biological samples are a tissue from ileum or colon, that permits confirmation of marked potentiation of the expression, more preferably a tissue from colon. Then, an mRNA or a protein is extracted from the sample. When an mRNA is extracted, an expression thereof is examined using the diagnostic reagent of the present invention which contains a probe, according to a method generally employed in the pertinent field, such as northern blot and the like. It is also possible to conduct RT-PCR and the like using the diagnostic reagent of the present invention which contains a primer pair. When a protein is extracted, an expression thereof is examined using the diagnostic reagent of the present invention which contains an antibody or a fragment thereof, according to a method generally employed in the pertinent field, such as immunoblot, western blot and the like.

Moreover, the presence or otherwise of the lesion observed in Crohn's disease can be known or the lesion can be identified by preparing a tissue sample from a tissue obtained from a diagnosis target and subjecting the sample to tissue staining using the diagnostic reagent of the present invention which contains a probe or an antibody.

When the expression of the gene or protein examined as mentioned above is high, the animal is diagnosed as having developed Crohn's disease or having a high likelihood of developing Crohn's disease. When an accurate judgment is desired, comparison with the expression at the site (e.g., small intestine) expected to show no potentiation of the expression of the above series of genes or proteins, which are characteristic of Crohn's disease, is desirable.

According to the present invention, the aforementioned diagnostic reagent of the present invention and other reagents necessary for various methods using the inventive reagent, and the like are preferably packaged in combination to give a kit. For example, when the expression at the gene level is to be analyzed, a reagent for isolating the gene from a biological sample, such as surfactant, protease etc., buffer and the like may be contained in the kit. When the expression at the protein level is to be analyzed, for example, a reagent for extracting the protein from a biological sample, buffer and the like, and where necessary, a secondary antibody, a color developer reagent and the like may be contained in the kit.

It is also possible to construct a screening system of a pharmaceutical agent useful for Crohn's disease using the diagnostic reagent of the present invention and the principle of the diagnostic method of the present invention.

For this screening system, any cell population can be used as long as it can be treated with a pharmaceutical agent and it affords observation of changes in the expression of the aforementioned gene or protein specific to Crohn's disease. Specifically, a tissue derived from a target animal, animal other than human (mouse, rabbit and the like), cells of various primary cultures or established cell lines and the like are used. This tissue is appropriately determined depending on the main expression site of the target gene. A tissue is obtained or prepared from a given animal, treated with a given pharmaceutical agent for screening, and expression of at least one or all of PP6 regulated by IL-2, its gene, TNIK, its gene, FLIP, its gene, GRα, its gene, cytochrome oxidase subunit I, its gene, cytochrome b and its gene in the tissue is analyzed. The expression at the protein level and that at the gene level can be determined in parallel, whereby the action mechanism of the pharmaceutical agent for the screening can be postulated.

The present invention is explained in detail by referring to examples. The present invention is not limited by these examples in any way.

EXAMPLE 1

Identification of the Gene that Shows Lesion Specific Potentiation of Expression 1. Test Material and Test Method The lesion and non-lesion of one Crohn's disease descending colon excision specimen (excised in a surgical operation at Social Health Insurance Medical Center (Tokyo, Japan)) were analyzed by a differential display method (Delta Differential Display Kit, Clontech, CA). The total RNA from the tissues of both sites was extracted using a TRIZOL reagent (Life Technologies, MD) following the manual attached thereto. First-strand cDNA was then synthesized from 3 µg of total RNA using 1.5 µg oligo $(dT)_{15}$ primer, 1 mM dNTP mix, and 300 unit MMLV reverse transcriptase (Clontech, CA) in a final volume of 15 µl at 42° C. for 1 hour followed by the incubation at 75° C. for 10 min.

PCR for differential display method was carried out with anchored oligo (dT) 29-mer (T primers) and non-specific 5' oligonucleotide 25-mer (P primers) (both from Clontech). Ten kinds of P primers and 9 kinds of T primers were appropriately combined to give 90 combinations of different non-specific PCR primer pairs, and using the primer pairs, cDNA was amplified. That is, cDNA synthesized from 0.01 or 0.0025 μg of the total RNA was mixed with 50 μM dNTP mix (Clontech), 1 μM P primer, 1 μM T primer, and Advantage KLENTAQ® Polymerase mix (50X) (Clontech) in a final volume of 10 μl, and was PCR amplified under the following conditions (Thermal cycler MP, Takara).

The first three cycles of PCR were done under low stringency conditions;
94° C., 5 min→40° C., 5 min→68° C., 5 min (1 cycle)
94° C., 30 sec→40° C., 30 sec→68° C., 5 min (2 cycles).

The obtained product was subjected to the remaining cycles under high stringency conditions;
94° C., 20 sec→60° C., 30 sec→68° C., 1 min (30 cycles).

The amplified cDNAs were loaded on a 6% denaturing standard sequencing polyacrylamide gel (Roche Molecular Biochemicals-Boehringer, Mannheim) and were separated according to the fragment size and visualized by silver staining (Promega, Wis.).

2. Results

Upon silver staining, the non-lesion site and the lesion site showed clear difference in the pattern.

3. Identification of the gene that shows lesion specific potentiation of expression The band positively detected in the lesion by silver staining was cleaved out and the DNA was extracted, which was followed by amplification using the same primer. Since the cleaved band contained multiple gene fragments of the same size, the amplified fragments were then fractionated using SSCP method (Hatta, Y, et al., Immunogenetics 49:280–286 (1999)).

Reamplified PCR products were cloned into the pCR-TOPO vector (TOPO TA cloning kit, Invitrogen, Netherlands) and subjected to fluorescence-based automated cycle sequencing (ABI310, Applied Biosystems, Foster city, Calif.) using dye-terminator method according to the manual (ABI PRISM™ dRhodamine Terminator Cycle Sequencing-Ready Reaction Kit). Homology search was performed using EMBL/GenBank database and the NCBI BLAST program (National Library of Medicine, Bethesda, Md.).

As a result, potentiation of the expression of PP6 regulated by IL-2 mRNA, TNIK mRNA, FLIP mRNA, GRα mRNA, cytochrome oxidase subunit I mRNA and cytochrome b mRNA was newly confirmed in Crohn's disease intestinal tissue.

EXAMPLE 2

Semi-quantitation RT-PCR

1. Test Material and Test Method

The total RNA was extracted from the lesion and non-lesion of six Crohn's disease descending colon excision specimens (excised in a surgical operation at Social Health Insurance Medical Center (Tokyo, Japan)) using a TRIZOL reagent (Life Technologies, Md.) following the manual attached thereto. First-strand cDNA was then synthesized from 3 μg of total RNA using 1.5 μg oligo (dT)$_{15}$ primer, 1 mM dNTP mix, and 300 unit MMLV reverse transcriptase (Clontech, Calif.) in the final volume of 15 μl at 42° C. for 1 hour, followed by incubation at 75° C. for 10 min. Using the obtained 1st strand cDNA as a template, semi-quantitative RT-PCR was conducted. As a control, GAPDH mRNA was used. Using the respective primer pairs as shown in Table 1, GENEAMP® reagents and AMPLITAO GOLD® DNA polymerase (Perkin-Elmer, Norwalk, Conn.), PCR amplification was performed (Thermal cycler MP, Takara).

TABLE 1

| | Chromosomal location | Size of PCR product | Primer (sense) | Primer (antisense) | Annealing temperature |
|---|---|---|---|---|---|
| PP6 regulated by IL-2 | Not identified | 413 | ACCCATTTTTCTGCCCTCTT (SEQ ID No.1) | TCGTGCCCACTGAATAACAA (SEQ ID No.2) | 50° C. |
| TNIK | Not identified | 184 | TGGTTCACACACTGGTTTCC (SEQ ID No.3) | CCGGCCATAGGTGTTTACAT (SEQ ID No.4) | 50° C. |
| FLIP$_L$ | 2q33-34 | 204 | CTCCAAGCAGCAATCCAAA (SEQ ID No.5) | GATTCCTAGGGGCTTGCTCT (SEQ ID No.6) | 50° C. |
| FLIPs | 2q33-34 | 203 | TGCCTAAAGAACATCCACAGAA (SEQ ID No.7) | CACATGGAACAATTTCCAAGAA (SEQ ID No.8) | 50° C. |
| GRα | 5q31 | 477 | CCTAAGGACGGTCTCAAGAGC (SEQ ID No.9) | GCCAAGTCTTGGCCCTCTAT (SEQ ID No.10) | 57° C. |
| Cytochrome oxidase subunit I | Mitochondria | 201 | ACGCACTCTCCCCTGAACT (SEQ ID No.11) | GGGGAATGCTGGAGATTGTA (SEQ ID No.12) | 50° C. |
| Cytochrome b | Mitochondria | 195 | CACATCAAGCCCGAATGATA (SEQ ID No.13) | GTCTGCGGCTAGGAGTCAAT (SEQ ID No.14) | 50° C. |

PCR Conditions
94° C., 10 min
94° C., 30 sec→annealing (30 sec, temperature shown in Table 1)→72° C., 30 min (30 cycles)
72° C., 10 min The resulting PCR products were electrophoresed on a polyacrylamide gel and stained with SYBR Gold (Eugene Oreg.). The PCR products were quantitatively determined using scanning densitametry (Molecular Imager FX, BIO-RAD, Hercules, Calif.).

The expression of each gene in the lesion and non-lesion of the six excision specimens (No. 1-No. 6) of the Crohn's disease descending colon was examined. The results in mRNA ratios are shown in Table 2.

significant gene involved in the disease has been found, the invention can be used for screening a pharmaceutical agent useful for Crohn's disease.

This application is based on a patent application No. 2000-162858 filed in Japan, the contents of which are hereby incorporated by reference.

TABLE 2

|  | Specimen 1 Inflamed (C)/ uninflamed (C) | Specimen 2 Inflamed (I)/ uninflamed (I) | Specimen 3 Inflamed (C)/ uninflamed (C) | Specimen 4 Inflamed (I)/ uninflamed (I) | Specimen 5 Inflamed (TI)/ uninflamed (TI) | Specimen 6 Inflamed (C)/ uninflamed (C)) |
| --- | --- | --- | --- | --- | --- | --- |
| GRα | 4/1 | 1.5/1 | 4/1 | 1/1 | 4/1 | 4/1 |
| Cytochrome b | 2/1 | 1/1 | 8/1 | 1/1 | 2/1 | 6/1 |
| Cytochrome oxidase subunit I | 1.7/1 | 1/1 | 8/1 | 1/1.5 | 2/1 | 8/1 |
| PP6 regulated by IL-2 | 3/1 | 2.7/1 | 8/1 | 2.7/1 | 1.7/1 | 3/1 |
| $FLIP_S$ | 12/1 | 1/1 | 8/1 | 1/1 | 3/1 | 2/1 |
| $FLIP_L$ | 10/1 | 2/1 | 8/1 | 1/1 | 3/1 | 16/1 |
| TNIK | 4/1 | 1/1 | 5/1 | 1/1 | 2/1 | 13/1 |

C: colonic, I: ileal, TI: terminal ileal

The potentiation of the expression of the gene of PP6 regulated by IL-2, TNIK gene, FLIP gene, GRα gene, cytochrome oxidase subunit I gene and cytochrome b gene was found in the lesion. The difference was particularly high in the colon.

EXAMPLE 3

Immunohistochemistry

1. Test Material and Test Method

The tissues of the lesion and non-lesion of one Crohn's disease descending colon excision specimen (excised in a surgical operation at Social Health Insurance Medical Center (Tokyo, Japan)) were immersed in 50% OCT (Tissue-Tek, Sakura Finetech, Torrance, Calif.)/PBS and snap-frozen in liquid nitrogen, and the specimen was preserved at -70° C. until use. Serial sections (thickness: 5 μm) were prepared from the frozen specimen, air-dried on a slide glass and fixed in acetone for 20 min. The sections were preincubated with PBS containing 5% hydrogen peroxide, and then incubated for 45 min with the first antibody. The antibody was a rabbit polyclonal antibody against epitope corresponding to amino acids 201-350 of human $FLIP_L$ (Santa Cruz, Calif.) diluted at 1:50 in PBS. After reaction with the first antibody, the sections were washed 3 times with PBS, incubated with peroxidase labeled goat anti-rabbit IgG antibody (Nichirei Corp.) for 30 min, and incubated with a color developer (Histofine simplestain PO[R], Nichirei Corp.) to allow coloring.

2. Results

The potentiation of the expression of $FLIP_L$ at the lesion was confirmed.

In the present invention, a gene that shows lesion-specific potentiation of expression was taken note of and the behavior thereof was examined, whereby an easy and quick diagnosis of Crohn's disease has been afforded. Since a

SEQUENCE LISTING FREE TEXT

| SEQ ID NO: 1 | Oligonucleotide designed to act as primer for RT-PCR of PP6 regulated by IL-2 mRNA. |
| --- | --- |
| SEQ ID NO: 2 | Oligonucleotide designed to act as primer for RT-PCR of PP6 regulated by IL-2 mRNA. |
| SEQ ID NO: 3 | Oligonucleotide designed to act as primer for RT-PCR of TNIK mRNA. |
| SEQ ID NO: 4 | Oligonucleotide designed to act as primer for RT-PCR of TNIK mRNA. |
| SEQ ID NO: 5 | Oligonucleotide designed to act as primer for RT-PCR of $FLIP_L$ mRNA. |
| SEQ ID NO: 6 | Oligonucleotide designed to act as primer for RT-PCR of $FLIP_L$ mRNA. |
| SEQ ID NO: 7 | Oligonucleotide designed to act as primer for RT-PCR of $FLIP_S$ mRNA. |
| SEQ ID NO: 8 | Oligonucleotide designed to act as primer for RT-PCR of $FLIP_S$ mRNA. |
| SEQ ID NO: 9 | Oligonucleotide designed to act as primer for RT-PCR of GRα mRNA. |
| SEQ ID NO: 10 | Oligonucleotide designed to act as primer for RT-PCR of GRα mRNA. |
| SEQ ID NO: 11 | Oligonucleotide designed to act as primer for RT-PCR of cytochrome oxidase subunit I mRNA. |
| SEQ ID NO: 12 | Oligonucleotide designed to act as primer for RT-PCR of cytochrome oxidase subunit I mRNA. |
| SEQ ID NO: 13 | Oligonucleotide designed to act as primer for RT-PCR of cytochrome b mRNA. |
| SEQ ID NO: 14 | Oligonucleotide designed to act as primer for RT-PCR of cytochrome b mRNA. |

What is claimed is:

1. A method for diagnosing Crohn's disease, which comprises the steps of (a) taking a biological sample from a human, the sample being obtained from colon tissue or ileum tissue, and (b) analyzing the level of gene expression of at least one gene selected from the group consisting of a gene encoding type 6 protein phosphatase regulated by interleukin 2, a gene encoding a Traf 2 and Nck interacting kinase, a gene encoding FLICE inhibitory protein and a gene encoding glucocorticoid receptor α, in the biological sample, wherein up-regulation of gene expression is an indicator of Crohn's disease, thereby diagnosing Crohn's disease.

2. The method for diagnosing Crohn's disease according to claim 1, which further comprises analyzing the level of gene expression of at least one gene selected from the group consisting of a gene encoding cytochrome oxidase subunit 1 and a gene encoding cytochrome b.

* * * * *